United States Patent
Kobilka et al.

(10) Patent No.: US 11,198,818 B2
(45) Date of Patent: Dec. 14, 2021

(54) BROMINATED FLAME-RETARDANT TETRAZINES

(71) Applicant: International Business Machines Corporation, Armonk, NY (US)

(72) Inventors: Brandon M. Kobilka, Fishkill, NY (US); Jason T. Wertz, Pleasant Valley, NY (US); Scott B. King, Rochester, MN (US); Jacob Porter, Highland, NY (US)

(73) Assignee: International Business Machines Corporation, Armonk, NY (US)

( * ) Notice: Subject to any disclaimer, the term of this patent is extended or adjusted under 35 U.S.C. 154(b) by 148 days.

(21) Appl. No.: 16/445,541

(22) Filed: Jun. 19, 2019

(65) Prior Publication Data

US 2020/0399540 A1 Dec. 24, 2020

(51) Int. Cl.
| | |
|---|---|
| *C07D 257/08* | (2006.01) |
| *C08K 5/3477* | (2006.01) |
| *C09K 21/10* | (2006.01) |

(52) U.S. Cl.
CPC ............ *C09K 21/10* (2013.01); *C07D 257/08* (2013.01); *C08K 5/3477* (2013.01)

(58) Field of Classification Search
CPC .................................................... C07D 257/08
See application file for complete search history.

(56) References Cited

U.S. PATENT DOCUMENTS

| | | |
|---|---|---|
| 8,349,923 B2 | 1/2013 | Roth |
| 9,315,617 B2 | 4/2016 | Meyer et al. |
| 2002/0086927 A1 | 7/2002 | De Schryver et al. |

FOREIGN PATENT DOCUMENTS

WO  WO-2017093263 A1 * 6/2017 .............. B01J 23/44

OTHER PUBLICATIONS

Mo et al., "Bioaccumulation of polybrominated diphenyl ethers, decabromodiphenyl ethane, and 1,2-bis(2,4,6-tribromophenoxy) ethane flame retardants in kingfishers (*Alcedo atthis*) from an electronic waste-recycling site in South China," Environmental Toxicology and Chemistry, vol. 31, No. 9, pp. 2153-2158, 2012.
Prokhorov et al., "Triazines, Tetrazines, and Fused Ring Polyaza Systems," Chapter 5.3, Progress in Heterocyclic Chemistry, vol. 2 5, pp. 391-408, 2013.
"Tetrazine," Tetrazine—an overview | Science Direct Topics, printed Dec. 4, 2018, 14 pages. https://www.sciencedirect.com/topics/chemistry/tetrazine.
"Pentabromobenzonitrile Reaction," SciFinder Results, 9 pages.
"Halogenated Tetrazine Background," SciFinder Results, 4 pages.
KOBILKA et al., "Organophosphorus Flame-Retardant Tetrazines," U.S. Appl. No. 16/298,300, filed Mar. 11, 2019.

* cited by examiner

*Primary Examiner* — Wenwen Cai
(74) *Attorney, Agent, or Firm* — Kelsey M. Skodje (57) ABSTRACT

A flame-retardant compound, a process for forming a flame-retardant compound, and an article of manufacture. The flame-retardant compound includes a tetrazine moiety and at least one ligand comprising a brominated moiety. The process includes providing starting materials, which include a nitrile compound, a bromine source, and hydrazine. The process also includes reacting the starting materials to form a tetrazine flame retardant. The article of manufacture includes a polymer and a flame-retardant compound having a tetrazine moiety and at least one ligand comprising a brominated moiety.

15 Claims, 10 Drawing Sheets

BROMINATED FLAME-RETARDANT TETRAZINES

BACKGROUND

The present disclosure relates to flame-retardant compounds and, more specifically, brominated flame-retardants.

Flame retardants include compounds that can be added to polymers in order to provide flame retardancy. These polymers can include materials such as plastics, foams, synthetic fibers, synthetic rubbers, etc. Examples of flame retardants include phosphorus-based flame retardants and brominated flame retardants (BFRs). BFRs are organic compounds having bromo substituents. Flame retardants in polymers can be broadly classified according to how the flame retardants are incorporated into a polymer matrix. Additive flame retardants are mixed into polymers during blending, curing, foaming, extrusion, or other processing techniques. Reactive flame retardants are bound at sites along the polymer chain, incorporated into the chain as comonomers, and/or used as cross-linkers.

SUMMARY

Various embodiments are directed to a flame-retardant compound. The flame-retardant compound includes a tetrazine moiety and at least one ligand having a brominated moiety, such as a hexabromocyclododecyl or brominated phenyl moiety. In some embodiments, the at least one ligand includes hexabromocyclododecyl and phenyl groups linked by an ether moiety (e.g., —O— or —$CH_2O$—). The at least one ligand can also include at least one brominated phenyl group. For example, the at least one ligand can be a pentabromophenyl, brominated diphenyl, or brominated diphenyl ether.

Additional embodiments are directed to a process, which includes providing starting materials and reacting the starting materials to form a tetrazine flame retardant. The starting materials include a nitrile compound, a bromine source (e.g., elemental bromine or an organobromide compound), and hydrazine. The process can also include incorporating the tetrazine flame retardant into a polymer, such as a polybutadiene or poly(ethylene-co-propylene-co-5-methylene-2-norbornene). The incorporating can include an inverse electron demand Diels-Alder reaction between the tetrazine flame retardant and a polymer having alkenyl moieties. Providing the starting materials can include providing a nitrile-substituted hexabromocyclododecane. In some embodiments, reacting the starting materials includes reacting the nitrile compound with the hydrazine to form a tetrazine compound, and reacting the tetrazine compound with the bromine source. In other embodiments, reacting the starting materials includes forming a brominated nitrile compound, and reacting the brominated nitrile compound with the hydrazine. Reacting the starting materials can also involve a Williamson ether synthesis.

Further embodiments are directed to an article of manufacture. The article of manufacture includes a polymer and a flame-retardant compound. The flame-retardant compound includes a tetrazine moiety and at least one ligand comprising a brominated moiety. The article of manufacture can also include an electronic component. In some embodiments, the polymer is a synthetic rubber or a polybutadiene. The flame-retardant compound can be covalently bound to the polymer.

DETAILED DESCRIPTION

Flame retardants are added to a wide variety of materials in order to ensure safety and protect the materials from damage. Examples of materials that often include flame-retardant additives include plastics, paints, coatings, foams, adhesives, synthetic fibers, acoustic dampening materials, insulation, and synthetic rubbers. Many of these materials are incorporated into electronics hardware (e.g., printed circuit boards (PCBs), integrated circuit packages, semiconductors, transistors, optoelectronics, capacitors, resistors, chip carriers, housings, etc.). For example, resins for PCBs can be made flame retardant by incorporating polymers (e.g., polybutadienes, epoxy resins, polyhydroxyurethane, polycarbonate, polyester, polyacrylate, polyimide, polyamide, polyurea, and/or poly(vinyl-ester) polymers) combined with flame retardants.

Flame retardants commonly used in the aforementioned applications include brominated compounds and organobromine compounds, which are also referred to as "brominated flame retardants (BFRs)." Flame retardants can be additive or reactive. Reactive flame retardants include functional groups capable of forming covalent bonds at one or more sites in a polymer matrix, being incorporated into the chain as comonomers, and/or being used as cross-linkers. Additive flame retardants are blended into polymers without binding.

Most BFRs are additive flame retardants. However, additive flame retardants leach out of materials more easily than reactive flame retardants. This can lead to bio-accumulation of the flame retardant and a reduction in flame retardancy over time. It has been necessary to reduce or eliminate the use of many BFRs due to their potential for bioaccumulation, environmental persistence, and toxicity. For example, the European Chemical Agency (ECHA) has issued guidelines limiting the use of some BFRs to less than 0.1%. Therefore, new flame retardants are needed to replace additive BFRs in polymer applications.

According to the present disclosure, polymers containing reactive brominated flame retardants having tetrazine moieties are formed. These flame retardants are referred to herein as "tetrazine flame retardants." Tetrazines are reactive cyclic structures that include a six-membered aromatic ring having four nitrogen and two carbon atoms. Tetrazines are used in click chemistry applications, as conjugation tags for materials chemistry, and in bioorthogonal chemistry. Tetrazines can also be used in high-energy materials and coordinating ligands. Substituted tetrazines are generally used in these applications, as the unsubstituted tetrazines are too unstable to be practical.

There are three families of tetrazines: 1,2,3,4-tetrazines, 1,2,3,5-tetrazines, and 1,2,4,5-tetrazines. Of these families, 1,2,4,5-tetrazines are the most commonly used. For example, 3,6-disubstituted 1,2,4,5-tetrazines react readily with alkenes. Tetrazine moieties in 3,6-disubstituted 1,2,4,5-tetrazines have the following structure:

where the dotted lines represent binding locations of the substituents (e.g. phenyl groups).

The tetrazine flame retardants disclosed herein are 3,6-disubstituted 1,2,4,5-tetrazines, wherein the substituents are organic ligands that include brominated moieties (e.g., brominated phenyl or cyclododecyl moieties). The tetrazine flame retardants are incorporated into polymers containing alkenyl groups (carbon-carbon double bonds) as reactive flame-retardants. Reactions between the tetrazine and alkenyl moieties (e.g., inverse electron demand Diels-Alder reactions) form covalent bonds between the flame retardants and polymers. For example, the brominated tetrazine flame retardants can act as crosslinkers in a polymer matrix.

Figure 1:
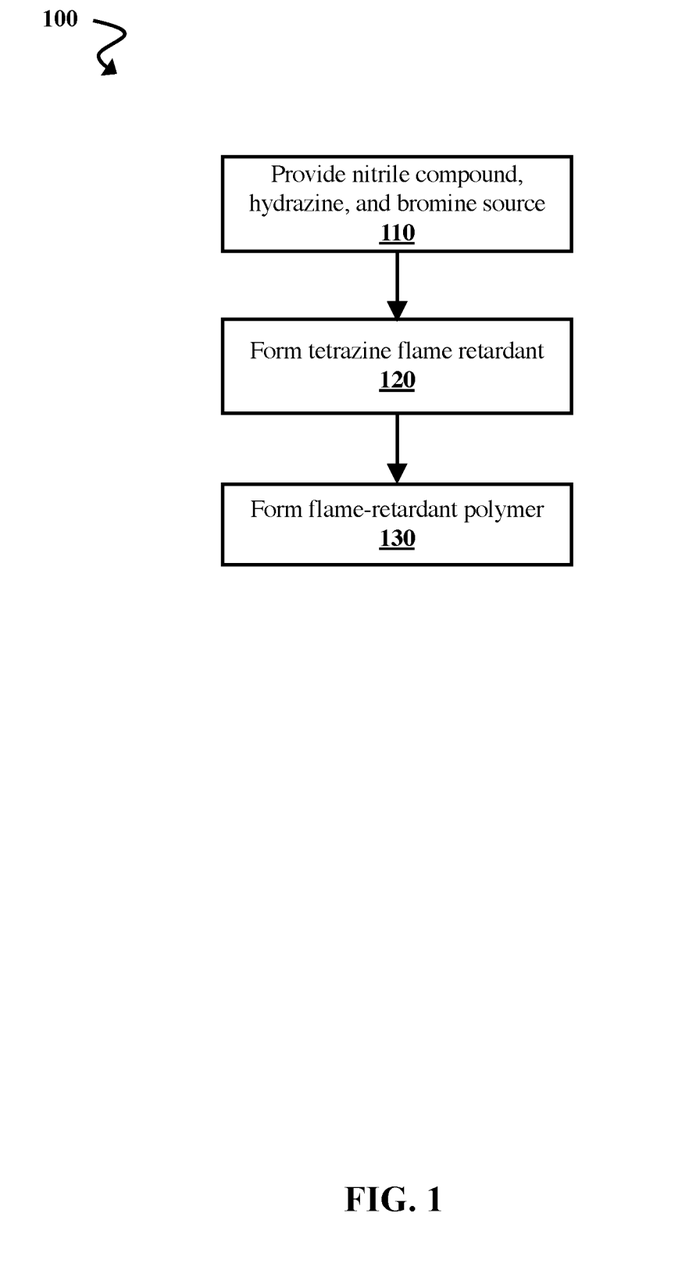
FIG. 1 is a flow diagram illustrating a process of forming a flame-retardant polymer, according to some embodiments of the present disclosure.

FIG. 1 is a flow diagram illustrating a process 100 of forming a flame-retardant polymer, according to some embodiments of the present disclosure. Starting materials for a reaction to form a flame-retardant tetrazine compound are provided. This is illustrated at step 110. The starting materials can be obtained from commercial sources, research institutions, or synthesized in situ. The starting materials can include hydrazine (NH$_2$NH$_2$), which can be provided as a hydrazine monohydrate (NH$_2$NH$_2$.H$_2$O) solution (e.g., an aqueous solution of approximately 64%, 78-82%, or 24-26% hydrazine), a source of bromine (e.g., elemental bromine (Br$_2$) or an organobromide having a functional group such as hydroxyl (—OH), iodo (—I), or chloro (—Cl)), and an aromatic compound or cycloalkene (e.g., cyclododecatriene) having a nitrile (—CN) functional group (referred to herein as "nitrile compounds" or "nitriles"). Examples of aromatic nitriles can include 4-hydroxybenzonitrile, 4-iodobenzonitrile, 4-(chloromethyl)benzonitrile, biphenyl nitrile, biphenyl ether nitrile.

In some embodiments, a single starting material (e.g., a brominated nitrile) is both the nitrile and the bromine source. Additionally, the nitrile and hydrazine starting materials can be provided as components of a compound having a tetrazine moiety (e.g., a substituted diphenyl tetrazine) obtained from a commercial source or prepared by another entity. It should also be noted that, while the flame retardants illustrated herein are brominated flame retardants, other halogenated flame retardants can be formed when the bromine source is replaced by another halogen (e.g., elemental chlorine (Cl$_2$) or an organochloride).

The starting materials are reacted to form a brominated tetrazine flame retardant. This is illustrated at step 120. Herein, brominated tetrazine flame retardants are also referred to as "tetrazine flame retardants". Various routes to forming tetrazine flame retardants can be used, which can involve the formation of different intermediates. However, each technique involves formation of a tetrazine moiety, as well as a bromination reaction or a substitution reaction with an organobromide. This provides the tetrazine compound with brominated ligands. In some embodiments, brominated nitriles are formed before formation of the tetrazines. In other embodiments, the tetrazines are formed prior to bromination or binding of an organobromide moiety.

The tetrazine flame retardants can then be incorporated into polymers. This is illustrated at step 130. The incorporation results in a flame-retardant polymer. A variety of flame-retardant polymers can be formed. The tetrazine flame retardants can be added in any appropriate amount, such as a weight percent (wt %) of about 0.01-0.99 wt %, about 1-5 wt %, about 4-8 wt %, about 5-20 wt %, or about 10-40 wt %. The amount of brominated tetrazine flame retardant incorporated into the polymer is selected based upon the intended flame retardancy and other properties (e.g., mechanical and/or electrical properties) of the polymer.

Figure 9:
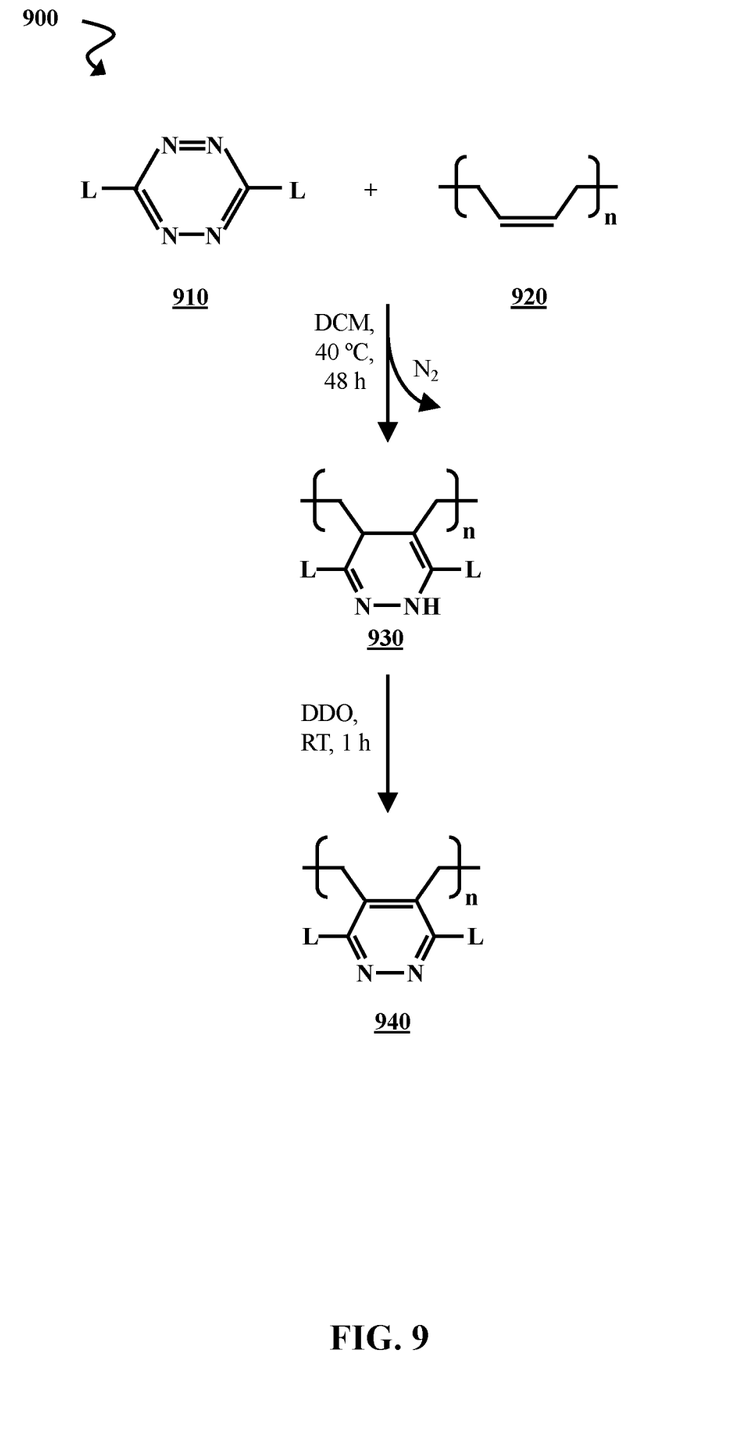
FIG. 9 is a chemical reaction diagram illustrating a process of incorporating brominated tetrazine flame retardants into polybutadiene, according to some embodiments of the present disclosure.
Figure 10:
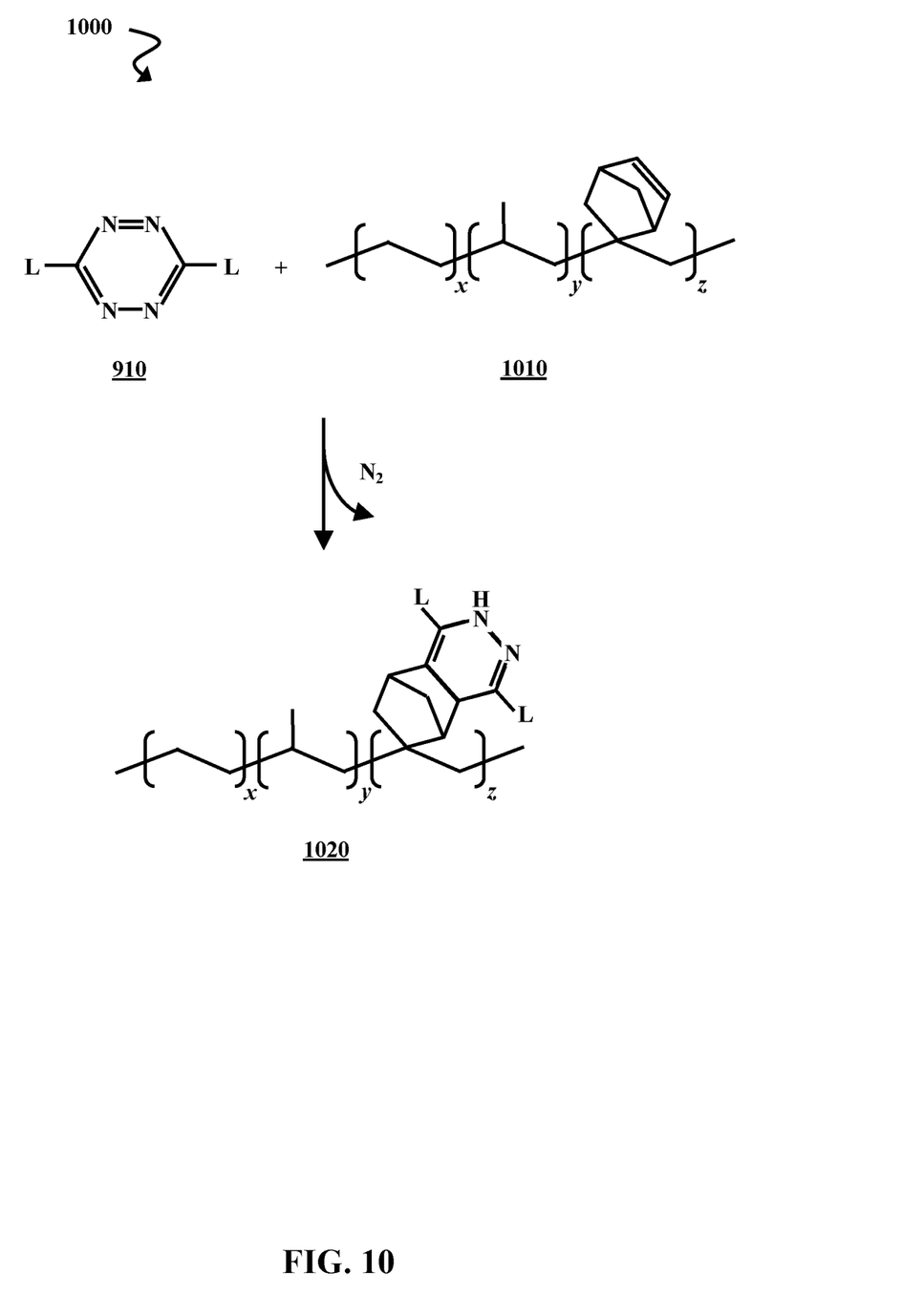
FIG. 10 is a chemical reaction diagram illustrating a process of incorporating brominated tetrazine flame retardants into an additional polymer, according to some embodiments of the present disclosure.

The brominated tetrazine flame retardants can be incorporated as reactive flame retardants. For example, polymers having alkene functional groups react readily with tetrazines by cycloaddition (e.g., in an inverse electron demand Diels-Alder reaction). Examples of these reactions are illustrated in FIGS. 9 and 10. Classes of polymer, prepolymer, or monomer that can react with the tetrazine flame retardants can include polybutadienes (e.g., a cis-, trans-, or cis/trans-polybutadiene, a predominately vinylic polybutadiene, a polycyclohexadiene, a polychloroprene, a poly-2-phenylbutadiene, a poly-isoprene, a poly(butadiene-block-styrene), polybutadienes having terminal nucleophilic groups such as a hydroxyl, thiol, or amine, a poly(butadiene-co-acrylonitrile), a poly(acrylonitrile-butadiene-styrene), etc.), synthetic rubbers (e.g., poly(ethylene-co-propylene-co-5-methylene-2-norbornene) or ethylene propylene diene monomer (EPDM) rubbers), acrylates with pendant or terminal alkenes, plant oils with unsaturated fatty acids, polyurethane prepolymer mixtures, etc.

The polymers can be homopolymers, block copolymers, random copolymers, or graft copolymers. Additionally, mixtures of two or more polymers can be used. In some embodiments, the brominated tetrazine flame retardants can also be incorporated as additive flame retardants. For example, a flame-retardant polymer can be formed by blending a brominated tetrazine flame retardant with a monomer solution, a bulk polymer, or a prepolymer. The blending can be carried out at room temperature or with heat.

Figure 2:
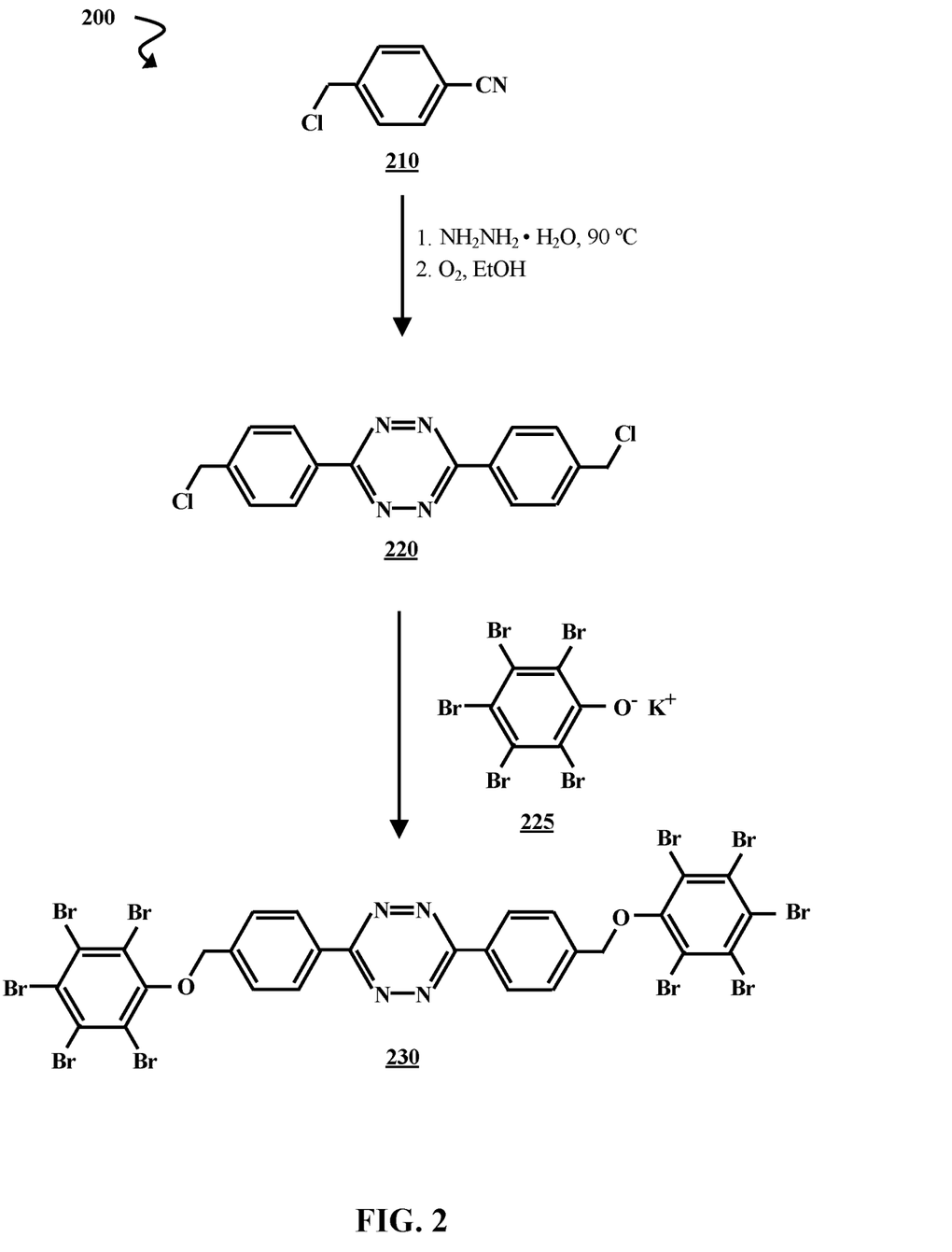
FIG. 2 is a chemical reaction diagram illustrating a process of forming a first brominated tetrazine flame retardant, according to some embodiments of the present disclosure.

FIG. 2 is a chemical reaction diagram illustrating a process 200 of forming a first brominated tetrazine flame retardant, according to some embodiments of the present disclosure. The nitrile starting material in process 200 is 4-(chloromethyl)benzonitrile 210. The 4-(chloromethyl) benzonitrile 210 is dissolved in hydrazine monohydrate ($NH_2NH_2 \cdot H_2O$) alone or in a mixture of $NH_2NH_2 \cdot H_2O$ and ethanol (EtOH). The resulting mixture is refluxed and/or heated at about 90° C. until a dihydrotetrazine intermediate (not shown) forms (e.g., approximately 10 hours (h)-20 h). Gaseous oxygen ($O_2$) is then bubbled through an EtOH solution or suspension of the dihydrotetrazine intermediate. In some embodiments, this oxidation reaction is carried out at an elevated temperature (e.g., about 50° C.) for about 3 h-10 h, though the temperature and duration of the reaction can be varied, as will be understood by a person of ordinary skill in the art. The oxidation of the dihydrotetrazine intermediate produces a tetrazine compound, bis-(chloromethyl) phenyl tetrazine 220.

A Williamson ether synthesis is then carried out on bis-(chloromethyl)phenyl tetrazine 220. Williamson ether syntheses are reactions between alkyl halides and alkoxides (e.g., the conjugate bases of hydroxyl compounds) to form ether linking groups. In this portion of process 200, bis-(chloromethyl)phenyl tetrazine 220 is reacted with potassium pentabromophenoxide 225. Potassium pentabromophenoxide 225 can be rapidly synthesized in situ by reacting Pentabromophenol with a potassium base (e.g., potassium hydroxide (KOH) or potassium t-butoxide). The reaction between bis-(chloromethyl)phenyl tetrazine 220 and potassium pentabromophenoxide 225 results in replacement of the chloro groups on the bis-(chloromethyl)phenyl tetrazine 220 with pentabromophenoxy substituents. The resulting flame-retardant compound 230 is referred to herein as "tetrazine flame retardant A 230".

Figure 3:
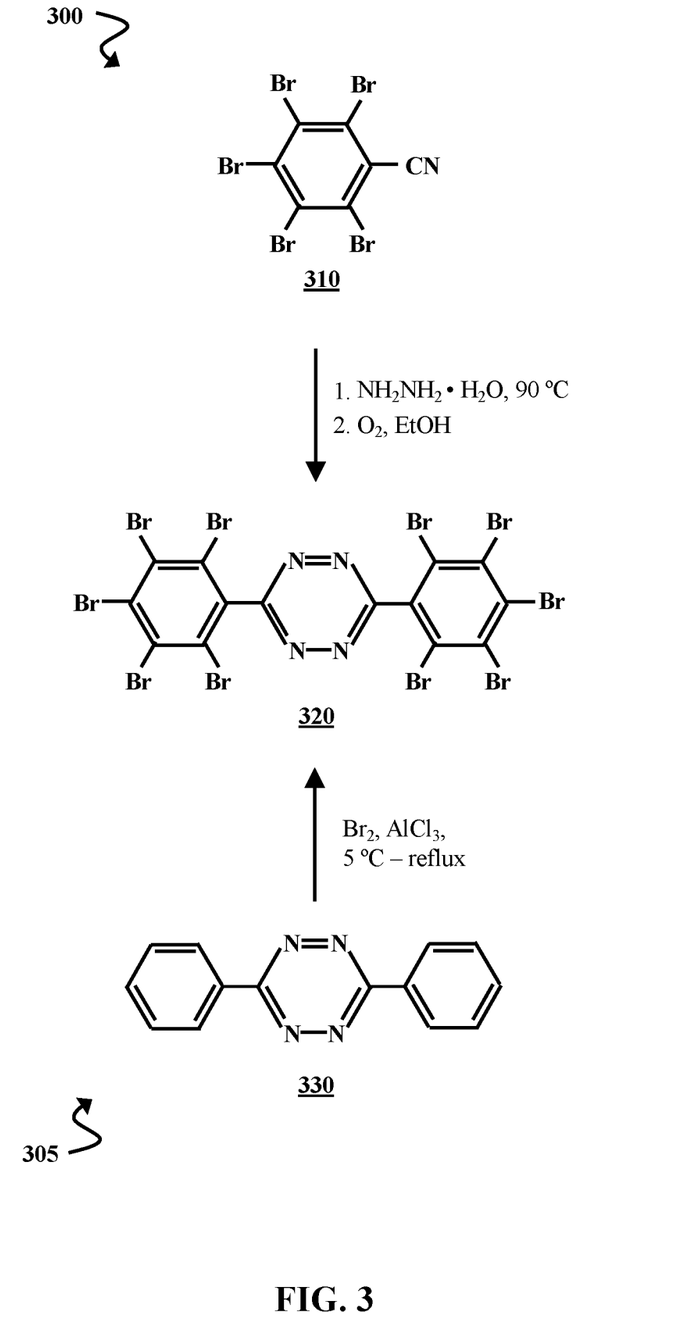
FIG. 3 is a chemical reaction diagram illustrating processes of forming a second brominated tetrazine flame retardant, according to some embodiments of the present disclosure.

FIG. 3 is a chemical reaction diagram illustrating processes 300 and 305 of forming a second brominated tetrazine flame retardant, according to some embodiments of the present disclosure. In process 300, pentabromobenzonitrile 310 is reacted with $NH_2NH_2 \cdot H_2O$ at about 90° C., followed by oxidation in EtOH. The reaction can be carried out using techniques substantially similar to those used to convert 4-(chloromethyl)benzonitrile 210 to bis-(chloromethyl)phenyl tetrazine 220 in process 200 (FIG. 2). This results in a decabromodiphenyl tetrazine 320 referred to herein as "tetrazine flame retardant B 320".

In process 305, a solution of 3,6-diphenyl-1,2,4,5-tetrazine 330 (e.g., in chloroform) is prepared. 3,6-Diphenyl-1, 2,4,5-tetrazine 330 can be obtained commercially or synthesized in a reaction between $NH_2NH_2 \cdot H_2O$ and 4-hydroxybenzonitrile (not shown), followed by oxidation (e.g., by $O_2$ in EtOH). The 3,6-diphenyl-1,2,4,5-tetrazine 330 solution is added dropwise to a mixture of bromine ($Br_2$) and anhydrous aluminum bromide ($AlBr_3$), which has been cooled to about 5° C. The reaction mixture is then heated to reflux, and allowed to proceed until the reaction is complete (e.g., ~1 h-12 h). The reaction can be carried out while refluxing, though lower temperatures can also be used (e.g., room temperature). Excess bromine can then be distilled off, and the solid product of the reaction can be washed with a ~5% solution of sodium sulfite ($Na_2SO_3$). From this product, tetrazine flame retardant B 320 can be extracted, filtered, and dried.

Figure 4:
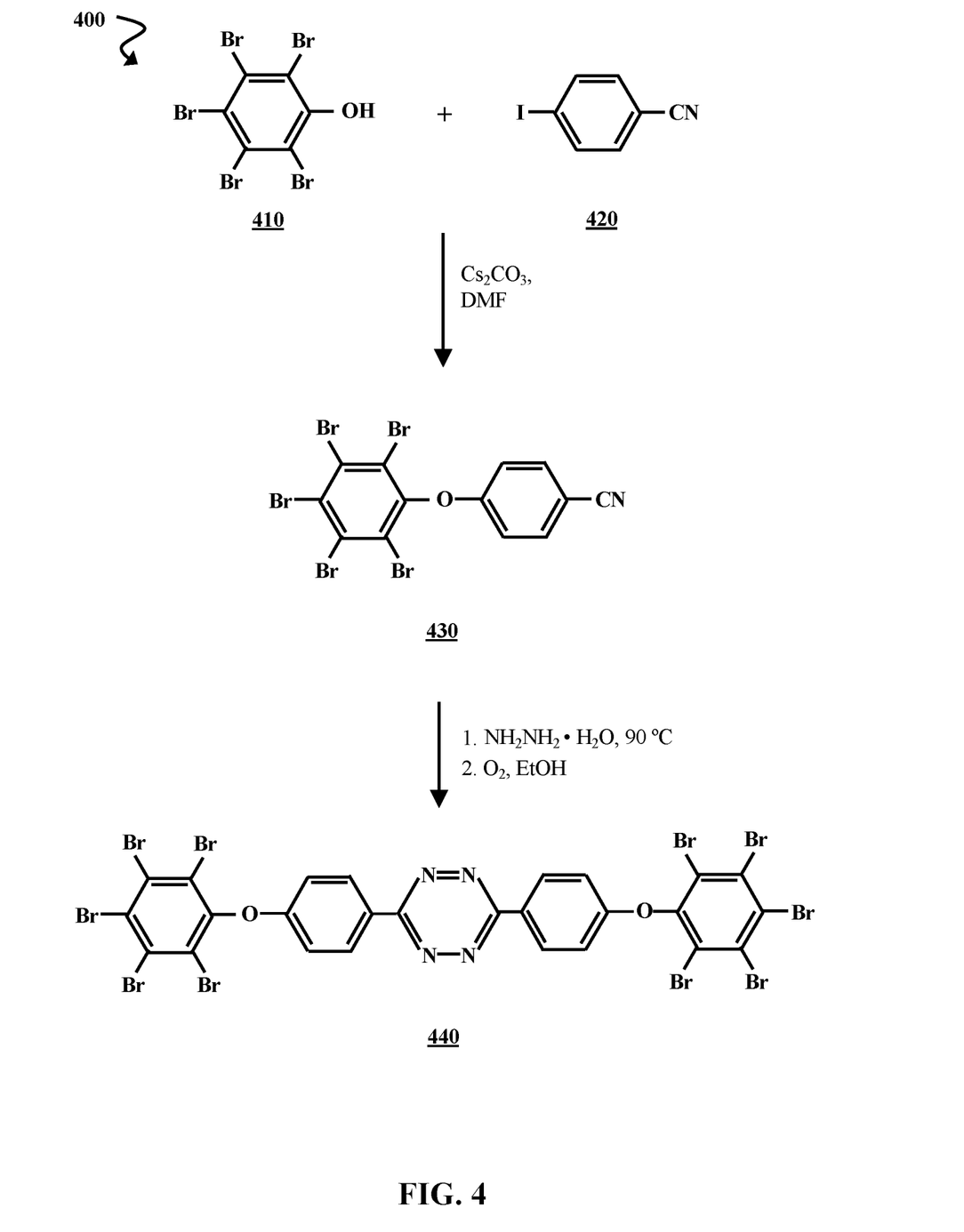
FIG. 4 is chemical reaction diagram illustrating a process of forming a third brominated tetrazine flame retardant, according to some embodiments of the present disclosure.

FIG. 4 is chemical reaction diagram illustrating a process 400 of forming a third brominated tetrazine flame retardant, according to some embodiments of the present disclosure. Pentabromophenol 410 is combined with 4-iodobenzonitrile 420 and cesium carbonate ($Cs_2CO_3$) in a room temperature dimethylformamide (DMF) solution. The solution can be heated to about 80° C. and reacted for approximately 24 h. However, the reaction can also be carried out at a lower temperature (e.g., room temperature) and/or another length of time (e.g., ~1 h, ~2 h, ~10 h, ~36 h, etc.). A nucleophilic aromatic substitution ($S_NAr$) reaction occurs between the reactants, resulting in a brominated nitrile, 4-pentabromophenoxybenzonitrile 430. A tetrazine moiety is formed via a reaction between 4-Pentabromophenoxybenzonitrile 430 and $NH_2NH_2 \cdot H_2O$ at about 90° C., followed by oxidation in EtOH. This reaction can be carried out using techniques substantially similar to those used in the first step of process 200 (FIG. 2). In process 400, the reaction results in the formation of a brominated tetrazine flame retardant 440 referred to herein as "tetrazine flame retardant C 440".

Figure 5:
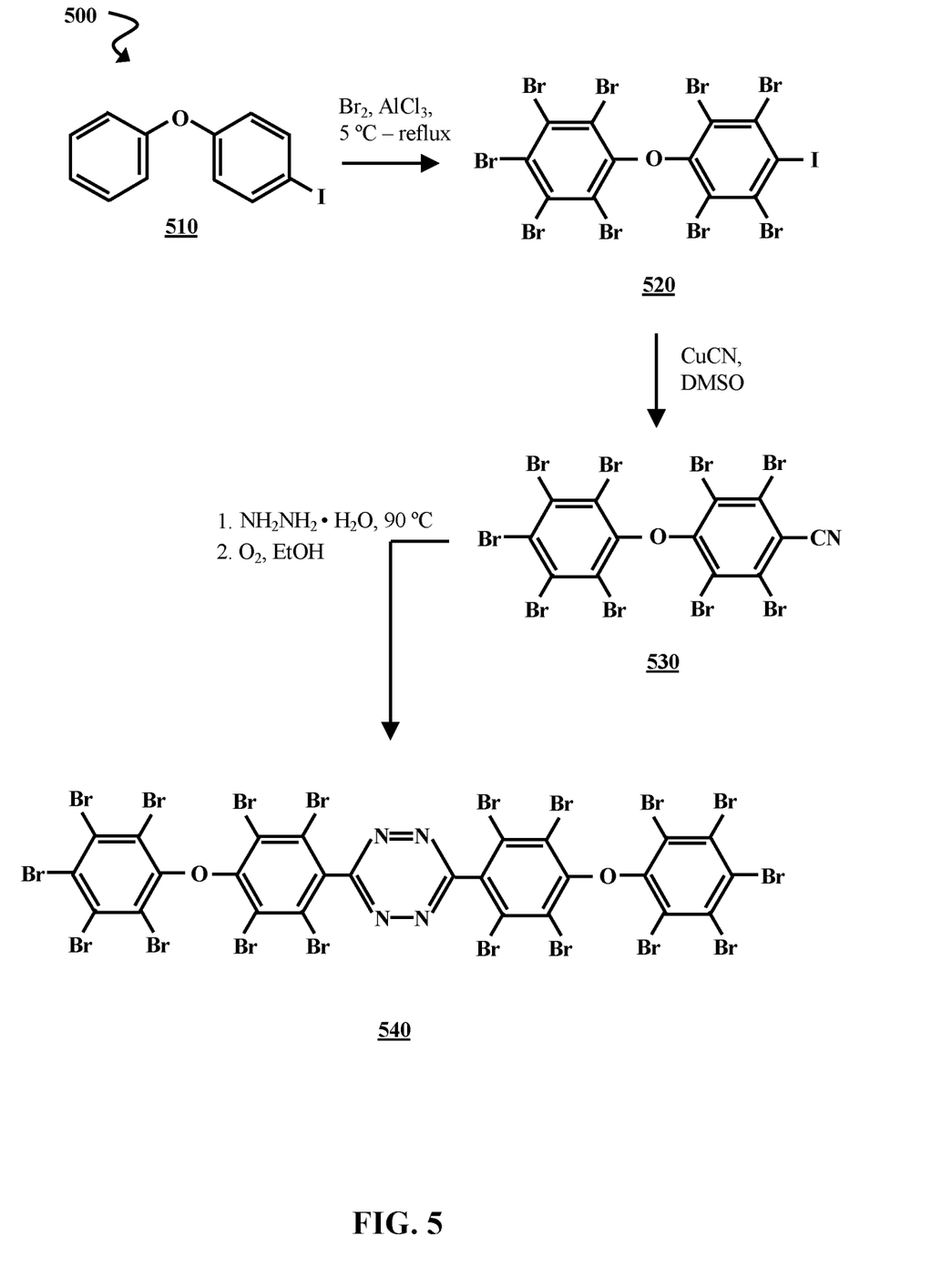
FIG. 5 is chemical reaction diagram illustrating a process of forming a fourth brominated tetrazine flame retardant, according to some embodiments of the present disclosure.

FIG. 5 is chemical reaction diagram illustrating a process 500 of forming a fourth brominated tetrazine flame retardant, according to some embodiments of the present disclosure. Process 500 begins with the bromination of 4-iododiphenyl ether 510 via reaction with $AlCl_3$ and $Br_2$. The bromination reaction can be carried out using techniques substantially similar to those used in the bromination reaction of process 305 (FIG. 3). This results in a brominated iododiphenyl ether 520. The brominated iododiphenyl ether 520 is reacted with copper(I) cyanide (CuCN) in dimethylsulfoxide (DMSO). This results in the formation of 2,3,5, 6-tetrabromo-4-(pentabromophenoxy)benzonitrile 530, which is then reacted with $NH_2NH_2 \cdot H_2O$ at about 90° C., followed by oxidation in EtOH. This reaction can be carried out using techniques substantially similar to those used in the first step of process 200 (FIG. 2). In process 500, the reaction results in the formation of a brominated tetrazine flame retardant 540 referred to herein as "tetrazine flame retardant D 540".

Figure 6:
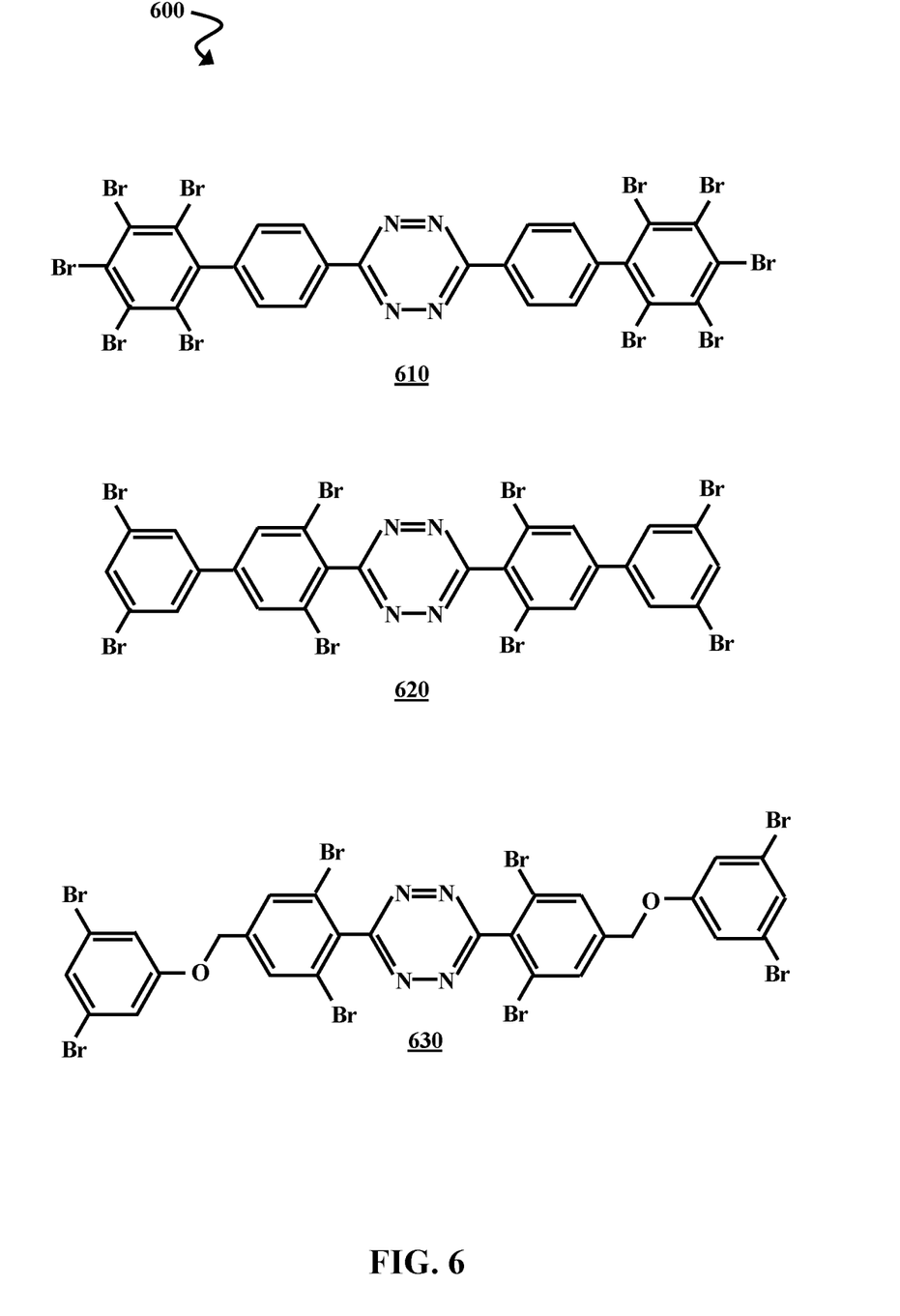
FIG. 6 is a chemical structure diagram illustrating structures of additional brominated tetrazine flame retardants that can be formed, according to some embodiments of the present disclosure.

FIG. 6 is a chemical structure diagram illustrating structures 600 of additional brominated tetrazine flame retardants that can be formed, according to some embodiments of the present disclosure. These brominated tetrazine flame retardants include tetrazine flame retardant E 610, tetrazine flame retardant F 620, and tetrazine flame retardant G 630. Tetrazine flame retardants E 610 and F 620 can be formed using techniques substantially similar to those of processes 300 (FIG. 3) and 500 (FIG. 5), and tetrazine flame retardant G 630 can be formed using techniques substantially similar to those of process 200 (FIG. 2). These and analogous brominated tetrazine flame retardants, can be formed via these techniques when the organobromide and/or nitrile starting compounds are varied.

For example, tetrazine flame retardant E 610 can be formed according to the techniques of process 300 when pentabromobenzonitrile 310 (FIG. 3) is replaced by 4-(pentabromophenyl)benzonitrile. Similarly, tetrazine flame retardant F 620 can be formed according to the techniques of process 300 when pentabromobenzonitrile 310 is replaced by 4-(3,5-dibromophenyl)-2,6-dibromobenzonitrile. Tetrazine flame retardant G 630 can be formed according to the techniques of process 200 when 4-(chloromethyl)benzonitrile 210 and potassium pentabromophenoxide 225 (FIG. 2) are replaced by 4-(chloromethyl)-2,6-dibromobenzonitrile and potassium 3,5-dibromophenoxide, respectively.

Examples of the aforementioned brominated nitriles and corresponding syntheses are not illustrated herein. However, brominated nitriles can be obtained through any suitable methods (e.g., synthesized in situ or obtained from another source). For example, a palladium-catalyzed Suzuki cross-coupling reaction between pentabromophenylboronic acid and 4-iodobenzonitrile can form 4-(pentabromophenyl)benzonitrile. In other embodiments, 4-(pentabromophenyl)benzonitrile can be formed in a palladium-catalyzed Suzuki cross-coupling reaction between 1,2,3,4,5-pentabromo-6-iodobenzene and 4-cyanophenylboronic acid pinacol ester. In another example, a palladium-catalyzed Suzuki cross-coupling reaction between 3,5-dibromophenylboronic acid and 2,6-dibromo-4-iodobenzonitrile can result in the formation of 4-(3,5-dibromophenyl)-2,6-dibromobenzonitrile. In other embodiments, 4-(3,5-dibromophenyl)-2,6-dibromobenzonitrile can be formed in a palladium-catalyzed Suzuki cross-coupling reaction between 3,5-dibromo-4-cyanophenylboronic acid pinacol ester and 1,3-dibromo-5-iodobenzene.

Reactants having different numbers of bromo substituents can optionally replace at least one of pentabromophenylboronic acid, 3,5-dibromophenylboronic acid, 4-iodobenzonitrile, 2,6-dibromo-4-iodobenzonitrile, 1,2,3,4,5-pentabromo-6-iodobenzene, 1,3-dibromo-5-iodobenzene, 4-cyanophenylboronic acid pinacol ester, and 3,5-dibromo-4-cyanophenylboronic acid pinacol ester in the Suzuki cross-coupling reactions. The resulting brominated nitriles can be used to make additional tetrazine flame retardants using techniques substantially similar to those illustrated herein, as will be understood by a person of ordinary skill in the art. Differences in the brominated tetrazine flame retardants (e.g., differences in the number of bromo and/or phenyl substituents) result in differences in the flame retardancy and other properties (e.g., reactivity and steric properties).

Figure 7:
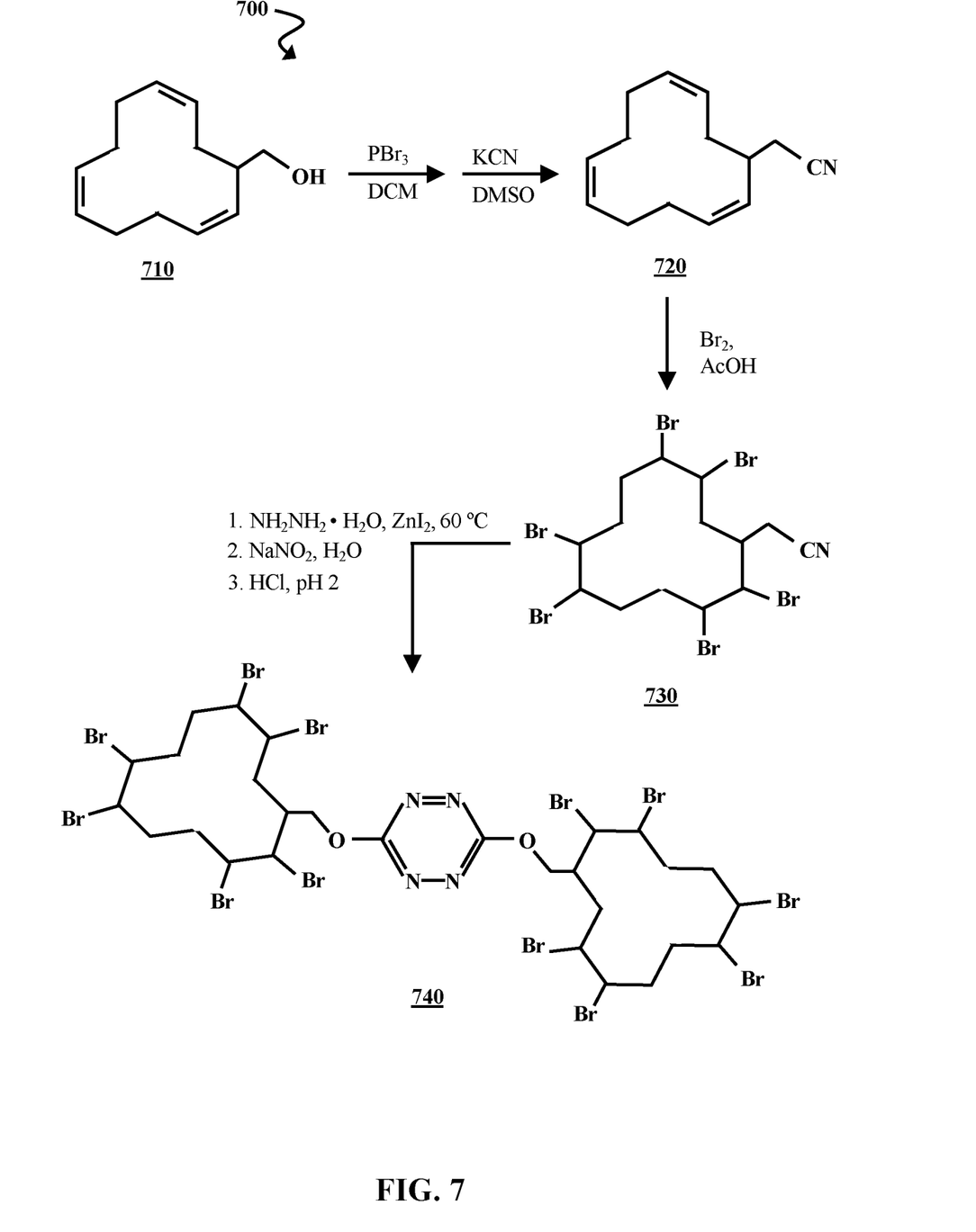
FIG. 7 is a chemical reaction diagram illustrating a process of forming a tetrazine flame retardant having brominated cyclododecyl moieties, according to some embodiments of the present disclosure.

FIG. 7 is a chemical reaction diagram illustrating a process 700 of forming a tetrazine flame retardant having brominated cyclododecyl moieties, according to some embodiments of the present disclosure. Process 700 can include a 4-hydroxymethyl-1,5,9-cyclododecatriene 710 starting material. Synthesis of 4-hydroxymethyl-CDT 710 is not illustrated in FIG. 7. However, this compound 710 can be formed by reacting 1,5,9-cyclododecatriene (CDT) with N-bromosuccinimide (NBS) to produce 4-bromo CDT, which is converted to a Grignard reagent and reacted with paraformaldehyde to produce the 4-hydroxymethyl-CDT 710. Process 700 continues with a reaction between 4-hydroxymethyl-CDT 710 and phosphorus tribromide (PBr$_3$) in dichloromethane (DCM), which replaces the hydroxyl substituent with a bromo substituent to form 4-bromomethyl CDT (not shown). However, in other embodiments, process 700 does not include the preceding steps. In these instances, 4-bromo CDT (not shown) is used as a starting material instead. In subsequent steps, this results in analogous compounds lacking methylene spacer groups in their respective substituents.

The mono-brominated compound (4-bromomethyl CDT or 4-bromo CDT) is then reacted with potassium cyanide (KCN) in DMSO to produce a nitrile compound. In the illustrated reaction, which involves 4-bromomethyl CDT, the nitrile compound formed is 4-cyanomethyl CDT 720. The 4-cyanomethyl CDT 720 is reacted with Br$_2$ in acetic acid (AcOH) to form a brominated nitrile, 4-cyanomethyl hexabromocyclododecane (HBCD) 730. The 4-cyanomethyl HBCD 730 is then reacted with hydrazine monohydrate and zinc iodide (ZnI$_2$) at about 60° C. for approximately 24 h. However, ZnI$_2$ can optionally be replaced by zinc trifluoromethanesulfonate (zinc triflate). The reaction mixture is cooled to room temperature, and an aqueous solution of sodium nitrite (NaNO$_2$) and, optionally, DMF is added. The reaction is completed by addition of aqueous HCl at room temperature until the reaction mixture reaches pH ~2-3. This results in a bis-hexabromocyclododecyl tetrazine flame retardant 740 ("tetrazine flame retardant H 740").

Figure 8:
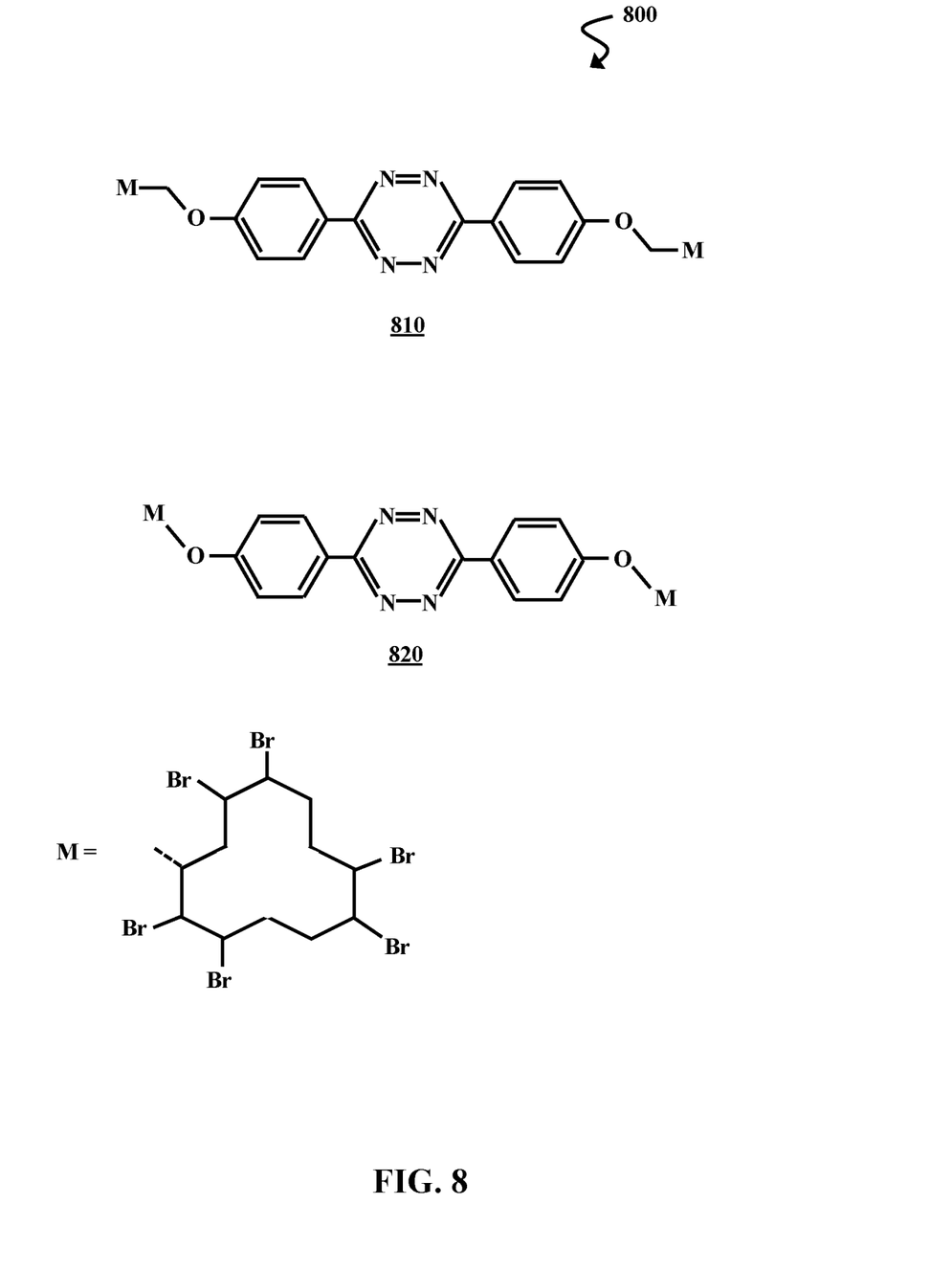
FIG. 8 is a chemical structure diagram illustrating structures of additional brominated cyclododecyl tetrazine flame retardants that can be formed, according to some embodiments of the present disclosure.

FIG. 8 is a chemical structure diagram illustrating structures 800 of additional brominated cyclododecyl tetrazine flame retardants that can be formed, according to some embodiments of the present disclosure. These brominated tetrazine flame retardants include tetrazine flame retardant I 810 and tetrazine flame retardant J 820, which have hexabromocyclododecyl moieties represented by M in the illustrated structures 800. Tetrazine flame retardants I 810 and J 820 are formed via Williamson ether syntheses in which the conjugate bases of 4-hydroxymethyl HBCD and 4-hydroxy HBCD, respectively, are reacted with 3,6-bis-(4-chlorophenyl)-1,2,4,5-tetrazine. These reactants are not illustrated herein. The reactions to form tetrazine flame retardants I 810 and J 820 can be carried out using techniques substantially similar to those of process 200 (FIG. 2).

FIG. 9 is a chemical reaction diagram illustrating a process 900 of incorporating brominated tetrazine flame retardants into polybutadiene, according to some embodiments of the present disclosure. The brominated tetrazine flame retardants described herein are collectively represented by a generic tetrazine flame retardant 910 having a tetrazine moiety and two L groups, which represent brominated ligands. Brominated tetrazine flame retardants that can be represented by tetrazine flame retardant 910 can include tetrazine flame retardants A 230, B 320, C 440, D 540, E 610, F 620, G 630, H 740, I 810, and J 820. These and other examples of tetrazine flame retardants that can be represented by tetrazine flame retardant 910 are discussed in greater detail with respect to FIGS. 2-8.

In process 900, tetrazine flame retardant 910 is reacted with polybutadiene 920 in an inverse electron demand Diels-Alder (or, "Carboni-Lindsey") reaction. However, other polymers having alkene moieties can be used instead of polybutadiene 920. Examples of these polymers are discussed in greater detail with respect to FIG. 1. The polybutadiene 920 can have any appropriate number (n) of repeat units. For example, n can be an integer between 1 and 1,000,000 (e.g., about 1-25,000, about 500-25,000, about 1,000-25,000, about 2,000-25,000, about 5,000-25,000, about 25,000-50,000, about 50,000-500,000, etc.). In some embodiments, the polybutadiene 920 has a number average molecular weight (M$_N$) between about 2,000 g/mol and 25,000 g/mol (e.g., about 4400 g/mol, about 10,000 g/mol, about 22,000 g/mol, etc.), though any conventional polybutadiene 920 can be used.

A mixture of tetrazine flame retardant 910 and polybutadiene 920 in DCM is prepared in an extruder or other reaction vessel. The mixture is degassed with argon for about 30 min, heated to about 40° C., and then refluxed for about 48 h or longer (e.g., about 72 h). The reaction produces nitrogen (N$_2$) gas, which can be vented into the atmosphere. However, the N$_2$ gas can also be used to produce a foam. In these instances, the reaction is carried out at room temperature for about 12 h-72 h.

The reaction between tetrazine flame retardant 910 and polybutadiene 920 produces a flame-retardant polybutadiene 930 having covalently-bound dihydropyridazine moieties with brominated ligands L. This flame-retardant polybutadiene is referred to herein as "dihydropyridazine polybutadiene 930". The number of flame-retardant moieties on dihydropyridazine polybutadiene 930 depends upon factors such as the reaction stoichiometry, temperature, duration, properties of tetrazine flame retardant 910 (e.g., bulkiness and number of bromo substituents), etc.

The solution containing dihydropyridazine polybutadiene 930 is cooled to room temperature (RT). A solution of dimethyl dioxirane (DDO) in acetone can be added to the room temperature mixture, which can then be stirred for about an hour. This oxidation reaction produces a flame-retardant polybutadiene 940 having covalently-bound pyridazine moieties with brominated ligands L ("pyridazine polybutadiene 940"). However, in other embodiments, the oxidation reaction is omitted from process 900. Instead, dihydropyridazine polybutadiene 930 can be isolated, and used as a flame-retardant material in various applications. Additionally, the dihydropyridazine amine group on dihydropyridazine polybutadiene 930 can be reacted further with functionalities such as epoxies, isocyanates, aldehydes, etc.

FIG. 10 is a chemical reaction diagram illustrating a process 1000 of incorporating brominated tetrazine flame retardants into an additional polymer, according to some embodiments of the present disclosure. The polymer is a synthetic rubber, poly(ethylene-co-propylene-co-5-methylene-2-norbornene) 1010, and the brominated tetrazine flame retardants are collectively represented by tetrazine flame retardant 910 (FIG. 9). The numbers of the repeat units in this rubber 1010 and the resulting flame-retardant polymer 1020 are represented by x, y, and z in FIG. 10, wherein x, y, and z are independently integers greater than 1. The number and order of repeat units can be varied, as will be understood by a person of ordinary skill in the art. For example, properties of the polymer 1010 (e.g., physical properties and number of alkenyl (—CH═CH—) binding sites for tetrazine flame retardant 910) can be varied by adjusting the relative values of x, y, and z. Increasing the value of z relative to x and y can provide more alkenyl groups that can bind tetrazine flame retardant 910. This can result in an increase in the polymer's flame retardancy.

The reaction between the tetrazine flame retardant 910 and poly(ethylene-co-propylene-co-5-methylene-2-norbornene) 1010 can be carried out using substantially the same techniques as those of forming dihydropyridazine polybutadiene 930 in process 900 (FIG. 9). This results in the production of a flame-retardant synthetic rubber 1020 having covalently-bound flame-retardant dihydropyridazine moieties. Further, flame-retardant synthetic rubber 1020 can be oxidized according to the techniques used to form flame-retardant polybutadiene 940 in process 900, though this step is not illustrated in FIG. 10. The flame retardancy of flame-retardant synthetic rubber 1020 can be adjusted by varying the norbornene (z) content of the poly(ethylene-co-propylene-co-5-methylene-2-norbornene) 1010 starting material, as well as by varying the reaction stoichiometry and/or properties of the flame retardant tetrazine 910 (e.g., bulkiness and number of bromo substituents) used in process 1000.

The compounds described herein can contain one or more chiral centers. Unless otherwise noted, the disclosed structures cover all stereoisomers, conformers, rotamers, isomers, and enantiomers of the represented compounds. Further, polymers or other materials containing the disclosed compounds can include racemic forms of the compounds in addition to individual stereoisomers, as well as mixtures containing any of these. Substituents on the tetrazine flame retardants and/or polymers described herein may participate in additional chemical reactions, transformations, or interactions, which can include synthesis, decomposition, single and/or double replacement, oxidation/reduction, acid/base, nucleophilic, electrophilic and radical substitutions, addition/elimination reactions, and polymerization reactions.

Where isomers of a named alkyl, alkenyl, alkoxy, aryl, or other functional group exist (e.g., n-butyl, iso-butyl, sec-butyl, and tert-butyl), reference to a member of the group without specifying a particular isomer (e.g., butyl) is intended to include all isomers in the family (e.g., n-butyl, iso-butyl, sec-butyl, and tert-butyl). Further, unless specified otherwise, reference to one member of the group (e.g., n-butyl) includes the remaining isomers in the family (e.g., iso-butyl, sec-butyl, and tert-butyl).

Unless otherwise noted, chemical reactions are performed at ambient conditions or under slight heating with no special atmosphere or head space, and may be performed using standard organic solvents to manage mix properties such as viscosity and flow index. Standard procedures for quenching reactions, solvent removal, and purification are performed. Room temperature is between about 15° C. and 25° C. unless otherwise indicated. Ranges (e.g., time, concentration, temperature, etc.) indicated herein include both endpoints and all numbers between the endpoints. Unless specified otherwise, the use of "about" or "approximately" in connection to a range applies to both ends of the range (e.g., "approximately 1 g-5 g" should be interpreted as "approximately 1 g-approximately 5 g"). Unless otherwise indicated, modifying terms such as "about" or "approximately" indicate +/−10% of a recited value, range of values, or endpoints of one or more ranges of values.

The processes discussed herein and their accompanying drawings are not to be construed as limiting. One skilled in the art would recognize that a variety of techniques may be used that vary in conditions, components, methods, etc., which ultimately generate brominated tetrazine flame retardants and flame-retardant polymers containing brominated tetrazine flame retardants. In addition, the conditions can optionally be changed over the course of a process. Further, in some embodiments processes can be added, omitted, or carried out in alternate orders, while still remaining within the scope of the disclosure, as will be understood by a person of ordinary skill in the art. It should also be noted that processes can be carried out by a single entity, or by multiple entities. For example, a first entity may produce the tetrazine flame retardants and a second entity may produce the flame-retardant polymers.

What is claimed is:

1. A flame-retardant compound, comprising:
   a tetrazine moiety; and
   at least one ligand comprising a brominated moiety selected from the group consisting of:

-continued wherein each dashed line represents a bond to a carbon atom in the tetrazine moiety.

2. A process, comprising:
providing starting materials, the starting materials comprising:
a nitrile compound;
a bromine source; and
reacting the starting materials to form a tetrazine flame retardant, the tetrazine flame retardant comprising:
a tetrazine moiety; and
at least one ligand comprising a brominated moiety selected from the group consisting of:

-continued wherein each dashed line represents a bond to a carbon atom in the tetrazine moiety.

3. The process of claim 2, wherein the bromine source is selected from the group consisting of elemental bromine and an organobromide compound.

4. The process of claim 2, wherein the reacting the starting materials comprises:
reacting the nitrile compound with the hydrazine to form a tetrazine compound; and
reacting the tetrazine compound with the bromine source.

5. The process of claim 2, wherein the reacting the starting materials comprises:
forming a brominated nitrile compound; and
reacting the brominated nitrile compound with the hydrazine.

6. The process of claim 2, wherein the reacting the starting materials comprises a Williamson ether synthesis.

7. The process of claim 2, further comprising incorporating the tetrazine flame retardant into a polymer.

8. The process of claim 7, wherein the polymer is a polybutadiene.

9. The process of claim 7, wherein the polymer is poly (ethylene-co-propylene-co-5-methylene-2-norbornene).

10. The process of claim 7, wherein the incorporating comprises an inverse electron demand Diels-Alder reaction between the tetrazine flame retardant and a polymer having alkenyl moieties.

11. An article of manufacture, comprising:
a polymer; and
a flame-retardant compound, comprising:
a tetrazine moiety; and
at least one ligand comprising a brominated moiety selected from the group consisting of:

-continued wherein each dashed line represents a bond to a carbon atom in the tetrazine moiety.

12. The article of manufacture of claim 11, further comprising an electronic component.

13. The article of manufacture of claim 11, wherein the polymer is a synthetic rubber.

14. The article of manufacture of claim 11, wherein the polymer is a polybutadiene.

15. The article of manufacture of claim 11, wherein the flame-retardant compound is covalently bound to the polymer.

* * * * *